United States Patent

Kuhlman et al.

[11] Patent Number: 5,857,218
[45] Date of Patent: Jan. 12, 1999

[54] PROTECTIVE VISOR FOR HAIR TREATMENT

[76] Inventors: Dennis Kuhlman, 12300 Cabana La., Austin, Tex. 78727; Eliseo Rodriguez, Jr., P.O. Box 2797, Cedar Park, Tex. 78630

[21] Appl. No.: 782,535

[22] Filed: Jan. 10, 1997

[51] Int. Cl.⁶ ................................................. A61F 9/00
[52] U.S. Cl. ................................ 2/174; 2/12; 2/200.1
[58] Field of Search .................... 2/12, 174, 200.2, 2/200.1, 209.3; 132/212

[56] References Cited

U.S. PATENT DOCUMENTS

| | | | |
|---|---|---|---|
| 2,282,220 | 5/1942 | Gage | 2/68 |
| 2,769,308 | 11/1956 | Krasno | 2/12 |
| 2,929,071 | 3/1960 | Sterling et al. | 2/68 |
| 2,987,730 | 6/1961 | Walker | 2/174 |
| 3,052,888 | 9/1962 | Blanchard | 2/68 |
| 4,335,471 | 6/1982 | Ouigley, Jr. et al. | 2/12 |
| 4,368,545 | 1/1983 | Seidman | 2/174 |
| 4,393,519 | 7/1983 | Nicastro | 2/12 |
| 4,481,680 | 11/1984 | Mason et al. | 2/174 |
| 4,945,575 | 8/1990 | Townsend | 2/12 |
| 4,958,385 | 9/1990 | Rushton | 2/174 |
| 5,023,954 | 6/1991 | Lyons | 2/174 |
| 5,423,091 | 6/1995 | Lange | 2/181 |

OTHER PUBLICATIONS

"Product Data Sheet"; Texas Fibers, Brenham, Texas; Oct. 15, 1996.
"Polyplastics"; Polyplastics, A Division of Buckley Industries, Inc., Austin, Texas.
"Microcell"; Sentinel Foam Products, a Division of Packaging Industries Group, Inc., Hyannis, MA.

*Primary Examiner*—Diana L. Biefeld
*Attorney, Agent, or Firm*—Steven D. Smit

[57] ABSTRACT

The present invention provides a protective visor for use during the treatment of hair comprising a bill attached to a headband, wherein the bill is composed of high density foam and the headband is composed of soft foam, the protective visor being adopted to attach to a person's head just below that person's hair line, thereby protecting that person from fluids running off of her hair or hot air blown in her face.

6 Claims, 3 Drawing Sheets

PROTECTIVE VISOR FOR HAIR TREATMENT

BACKGROUND OF THE INVENTION

1. Field of the Invention

Applicant's invention relates to the protection of a person's face and neck from liquids, chemicals and hot air during the preparation of that person's hair.

2. Background Information

Presently, the preparation of hair often requires the application of heat and chemicals which are uncomfortable to the person whose hair is being prepared. For instance, shampoos, conditioners and chemical applications such as hair dyes or permanents can run into the person's face when they are applied to the person's hair. Also, hair drying often requires the application of hot, dry air to the person's hair which air creates discomfort to the person's face, eyes, nose and mouth.

The hair preparation industry attempts to increase the comfort of the person whose hair is being treated by a number of primitive methods. For instance, the preparer will often hold a towel to the face of her client. Alternatively, the preparer will use her hand to divert the overflow of liquids or chemicals from her client's face. Often, the client is the one who must put a hand up to protect her own face. None of these methods are of much use in protecting a client's face during the hair drying process.

The hair preparation industry has attempted to alleviate the discomfort suffered by its clientele with a number of devices. For instance, U.S. Pat. No. 2,987,730 by Walker, discloses a cape-like protector with a transparent window which protects a person's face and shoulders during preparation of that person's hair, but which is cumbersome and uncomfortable to wear. Other devices, such as U.S. Pat. No. 5,423,091 by Lange, U.S. Pat. No. 4,958,385 by Rushton, and U.S. Pat. No. 5,023,954 by Lyons disclose the use of a headband comprised of absorbent material that absorbs liquids coming from the hair of a person; however, such devices tend to hold liquids against the person's skin, increasing the irritation caused by such liquids, and do not offer any protection from liquids splashing in the person's face. Still other devices, such as U.S. Pat. No. 4,481,680 by Mason et al., and U.S. Pat. No. 4,368,545 by Seidman disclose headband devices having a channel for liquids to escape from the person's hair; but these devices are unnecessarily complicated, and do not offer a secure guard for protection of a person's facial region.

The present invention attempts to increase the comfort and protection levels to a person whose hair is being prepared by providing an apparatus and method for diverting uncomfortable liquids, chemicals and blown air away from that person's face and neck.

BRIEF DESCRIPTION OF THE DRAWINGS

Applicant's invention may be further understood from a description of the accompanying drawings wherein, unless otherwise specified, like reference numbers are intended to depict like components in the various views.

DETAILED DESCRIPTION OF THE PREFERRED EMBODIMENT

The present invention increases the comfort of a person whose hair is being prepared by providing an apparatus and method which diverts fluids and blown air away from that person's face and neck. In its basic form, the invention provides a headband (20) which snugly conforms to the person's forehead and neck below the person's hairline. This allows a hair preparer to have full access to the person's hair, but creates a barrier which prevents fluids from flowing from the person's hair to her face and neck. A bill (10) is attached to the headband to form a visor over the person's forehead, thereby providing extra protection to the person's face, including protection from blown air.

Figure 1:
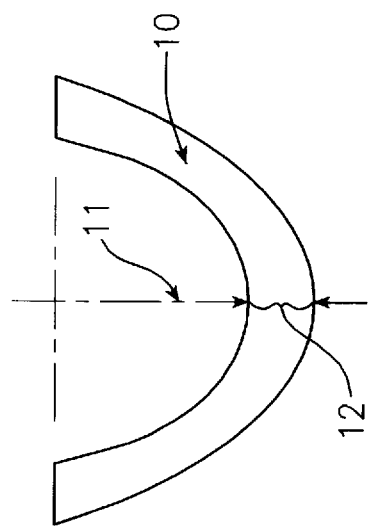
FIG. 1 is a top view of the preferred embodiment of the bill.

Referring now to FIG. 1, the preferred embodiment of the bill (10) is shown. Preferably, the bill (10) is formed of a high density foam in a semi-circle shape having a radius (11) approximately equal to the radius of a human's head. The inside of the semi-circle conforms approximately to the shape of a human's forehead. The bill has a width (12) that varies along the semi-circle shape. Preferably, the bill has a width of 3½" in its center, but this width narrows to 2" towards each end of the bill. This width provides maximum protection over sensitive facial features, while providing minimal interference over less-sensitive areas. However, any shape for the bill will suffice as long as the bill offers protection from the chemicals and heat applied during hair preparation. The bill extends downwardly from the headband preferably at an angle of approximately 45 degrees to allow any excess fluids in the person's hair to run away from the head before they drip down.

The bill (10) is preferably made of one-quarter inch thick Microcell Foam, sold under the designation MC1900 by Sentinel Foam Products located at 130 North Street, Hyannis, Mass., 02601. The Microcell Foam is a high density, closed cell, cross-linked polyethylene foam which does not absorb fluids and resists heat. The Microcell Foam is resilient and flexible, but the bill will support the weight of wet hair and light tools without bending. Other high density foams with similar specifications can be used as a replacement for Microcell Foam.

Figure 2:
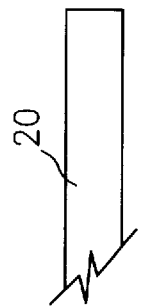
FIG. 2 is a side view of the preferred embodiment of the head band.
Figure 2:
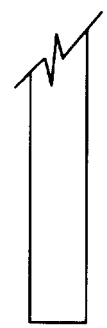

Referring to FIG. 2, the preferred embodiment of the headband (20) is depicted. The headband is formed of soft foam having a thickness of one square inch, and a length of approximately two feet long. The headband is preferably made of foam having the designation of 1030 which is sold by Texas Fibers located at 1200 Rink Street, Brenham, Tex. 77834. This 1030 foam, like the Microcell Foam used for the Bill, is also heat resistant and resilient, and does not absorb fluids. Other soft foams with similar specifications can be used as a replacement for this 1030 Foam.

Figure 4:
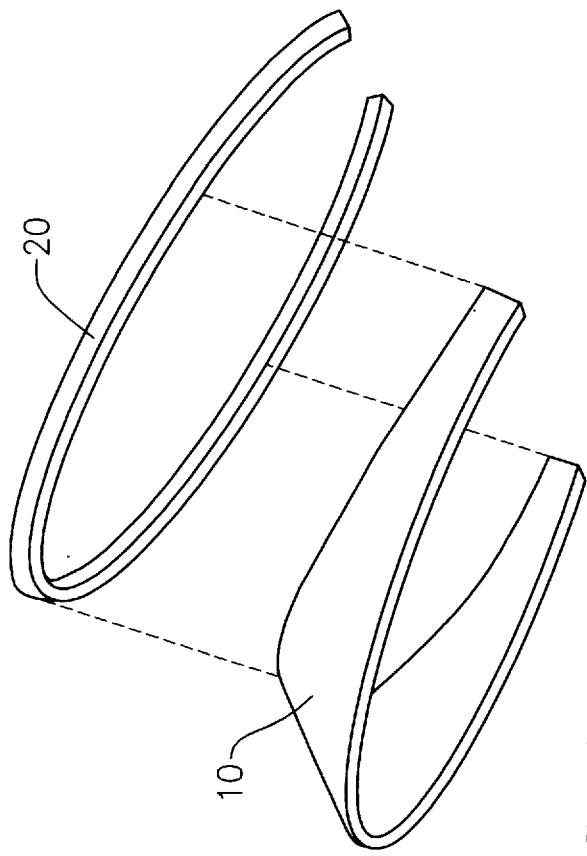
FIG. 4 is a perspective view of the preferred embodiment of the attachment of the bill to the head band.
Figure 3:
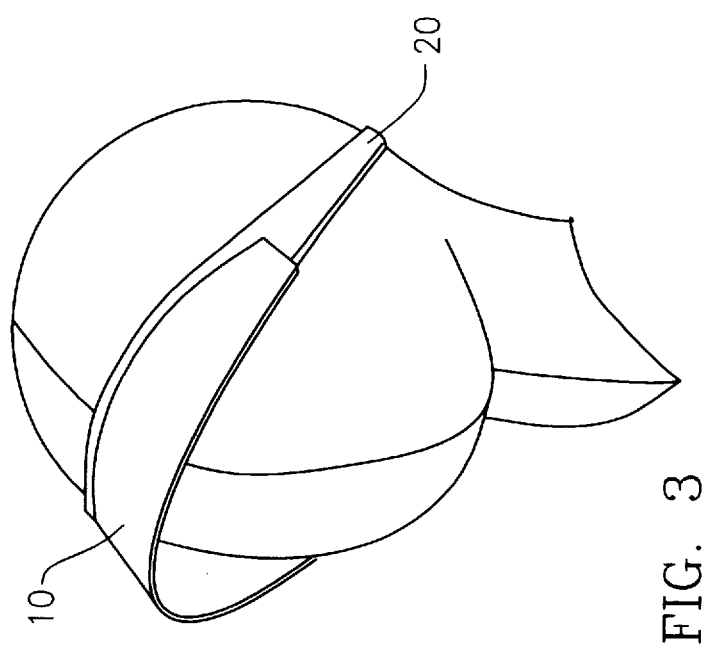
FIG. 3 is a side view of the preferred embodiment attached to a dummy.
Figure 5B:
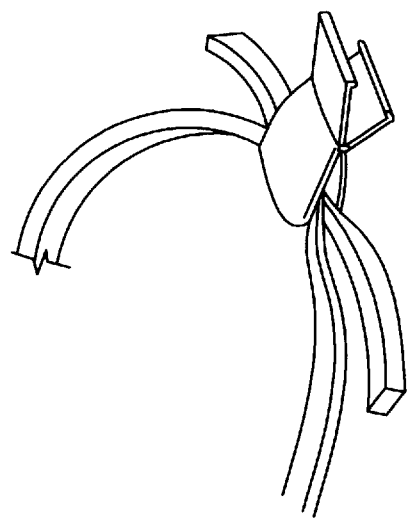
FIG. 5B is a side view of the preferred embodiment after the ends of the headband have been attached.
Figure 5A:
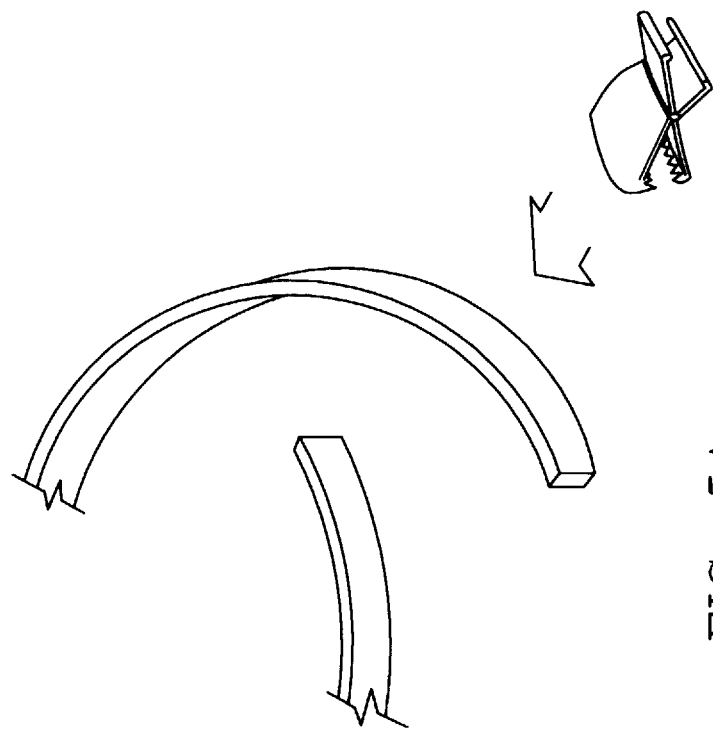
FIG. 5A is a side view of the preferred embodiment of attaching the ends of the headband.

In the preferred embodiment, the headband is glued to the bill (10) as depicted in FIG. 4 so that the ends of the headband extend past the ends of the bill. When the headband is placed on a person, as shown in FIG. 3, its ends meet at the back of the person's head, forming an overlap as is depicted in FIG. 5A. After the two ends of the headband are pulled together, thereby pulling the headband and bill snug against the person's head, they can be clipped together with an alligator clip, as is depicted in FIG. 5A and 5B.

In practice, the present invention can be utilized at any time during the preparation of hair by simply placing the headband on the person's head below that person's hair line and ears, and securing the invention with an alligator clip. The person can then have her hair prepared with greater comfort and safety. For instance, the person will enjoy a greater field of vision with which to read or converse with others or observe her hair being treated. Meanwhile, the preparer can use the bill as a rest for hair and tools without annoying the person. The easy connection of the ends of the headband with alligator clips, or other common means of connecting and holding together ribbons such as tying the ends together, allows the preparer to remove or replace the invention without disturbing the person or the hair. In an alternative form, to avoid the need for a clip, the headband can be one continuous piece of high density foam, instead of the non-continuous piece depicted in FIG. 2, which stretches to fit over the person's head and is then held in place by the resiliency of the foam. However, this alternative form makes attaching and removing the invention more difficult and bothersome.

The liquid-resistant and other qualities of the soft and high density foam offer many advantages. First, liquids are not retained against the skin of the person whose hair is being treated, thereby avoiding unnecessary exposure or irritation. Second, the protective visor does not become heavy as it would if it absorbed liquids, and thus remains comfortable and in place during hair treatment. In addition, the foams are inexpensive and disposable, and will not collect bacteria or molds that often grow in moist locations. Finally, the foams are resilient, thereby allowing a snug fit, but resist heat and maintain their shape during blow drying.

Although the invention has been described with reference to specific embodiments, this description is not meant to be construed in a limited sense. Various modifications of the disclosed embodiments, as well as alternative embodiments of the invention will become apparent to persons skilled in the art upon the reference to the description of the invention. It is, therefore, contemplated that the appended claims will cover such modifications that fall within the scope of the invention.

I claim:

1. A protective visor for hair treatment comprising:
    a headband comprised of a non-continuous piece of resilient soft foam having first and second ends, the soft foam being adapted to substantially repel liquids; and
    a bill comprised of a high density foam and extending downwardly from said headband.

2. The apparatus according to claim 1 further comprising attachment means for attaching the first end of said headband to the second end of said headband.

3. The apparatus according to claim 2 wherein said attachment means comprises an alligator clip.

4. A process for protecting a person's face during hair treatment comprising the steps of:
    attaching a protective visor to the person's head just below the person's hair line, wherein said protective visor comprises:
        a headband comprised of a soft foam that substantially repels liquids;
        a bill extending downwardly from said headband, said bill comprised of a high density foam; and
    preparing the person's hair.

5. The method according to claim 4 wherein:
    said headband separates to form first and second ends; and
    the protective visor is removably positioned on the person's head by fastening the first end to the second end.

6. The method according to claim 5 wherein said protective visor is attached to the person by clipping the first end to the second end with an alligator clip.

* * * * *